United States Patent [19]
Gat

[11] Patent Number: 5,954,663
[45] Date of Patent: Sep. 21, 1999

[54] FETAL MONITORING SYSTEM AND METHOD

[75] Inventor: Yigal Gat, Ramat Gan, Israel

[73] Assignee: Midas Medical Technologies Ltd., Tel Aviv, Israel

[21] Appl. No.: 08/859,146

[22] Filed: May 20, 1997

[30] Foreign Application Priority Data

May 22, 1996 [IL] Israel ........................................ 118389

[51] Int. Cl.[6] .................................................. A61B 5/0444
[52] U.S. Cl. ........................................................... 600/511
[58] Field of Search ................................... 610/453, 511, 610/588, 591; 128/903, 904

[56] References Cited

U.S. PATENT DOCUMENTS

| | | | |
|---|---|---|---|
| 4,086,917 | 5/1978 | Burks et al. .............................. | 600/453 |
| 5,431,171 | 7/1995 | Harrison et al. . | |
| 5,442,940 | 8/1995 | Secker et al. ............................ | 600/453 |

FOREIGN PATENT DOCUMENTS

| | | |
|---|---|---|
| 37 29 760 A1 | 9/1987 | Germany . |
| 3732122 A1 | 9/1987 | Germany . |
| WO 86/02250 | 4/1986 | WIPO . |
| WO 93/18710 | 9/1993 | WIPO . |

*Primary Examiner*—William E. Kamm
*Attorney, Agent, or Firm*—Mark M. Friedman

[57] ABSTRACT

A system and method for monitoring the condition of at least one fetus is provided. The fetal monitoring system includes a plurality of fetal well-being sensors, each of which detects signals during a monitoring period. The system also includes at least one interface unit, a central processing unit connected to the interface unit and a monitoring unit connected to the central processing unit. The interface unit is connected to the fetal well-being sensor for transmitting the detected signals. The central processing unit includes means for receiving and processing the signals. The monitoring unit enables the medical staff to monitor the transmitted and processed signals.

12 Claims, 12 Drawing Sheets

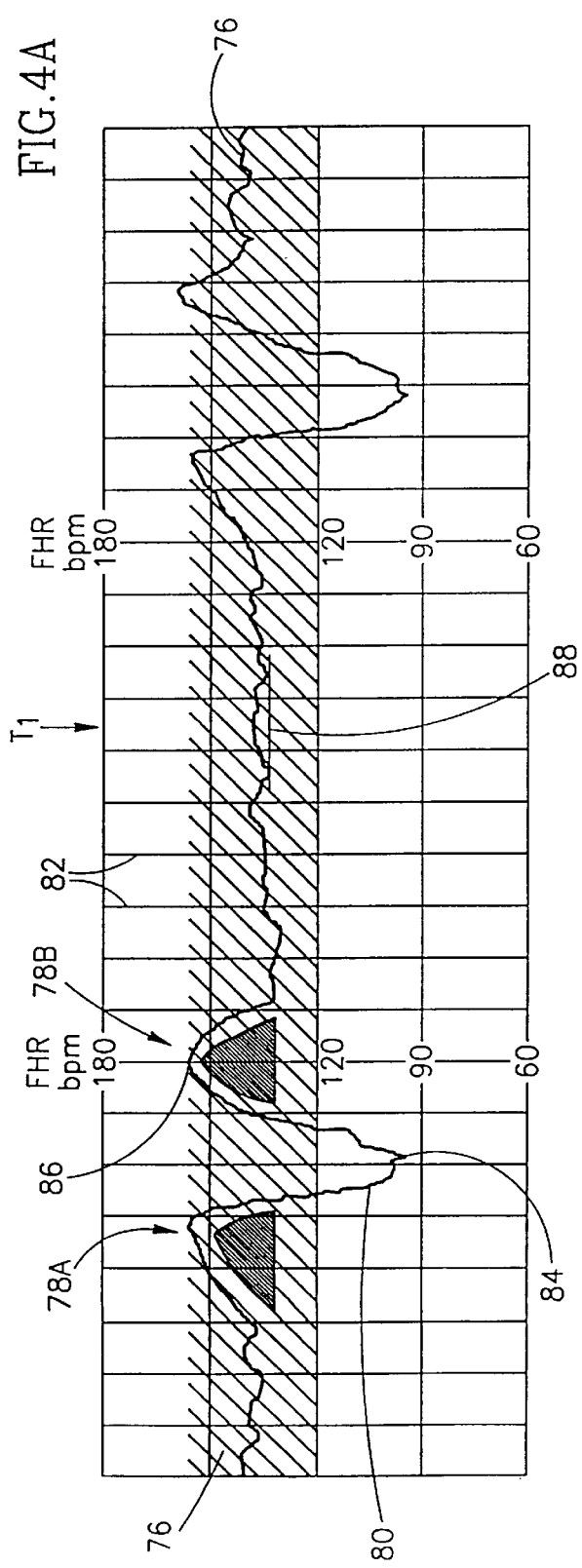
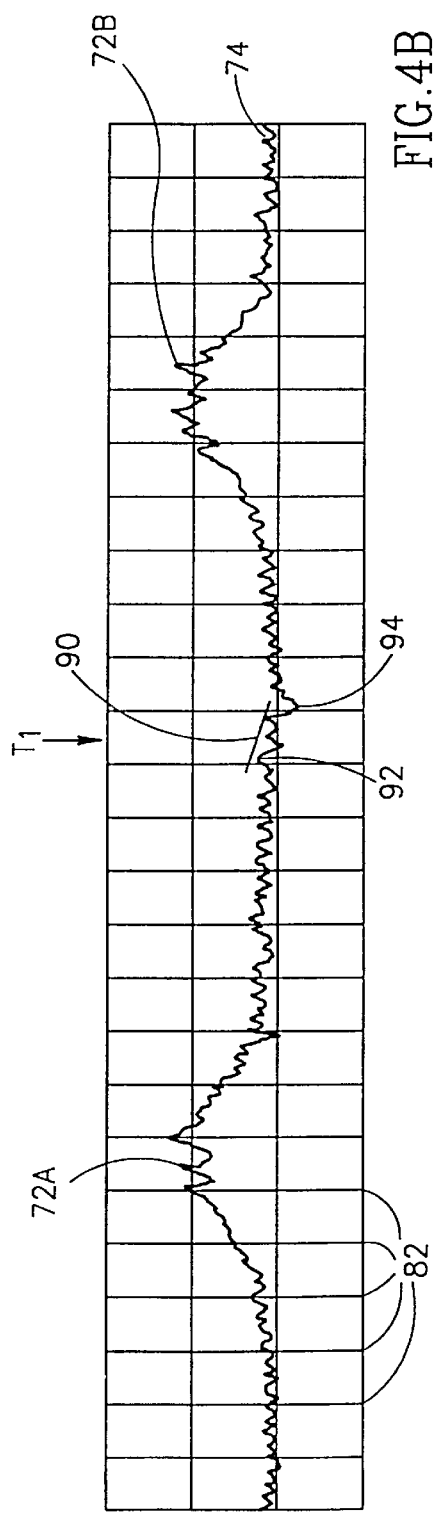
FIG. 4A
FIG. 4B

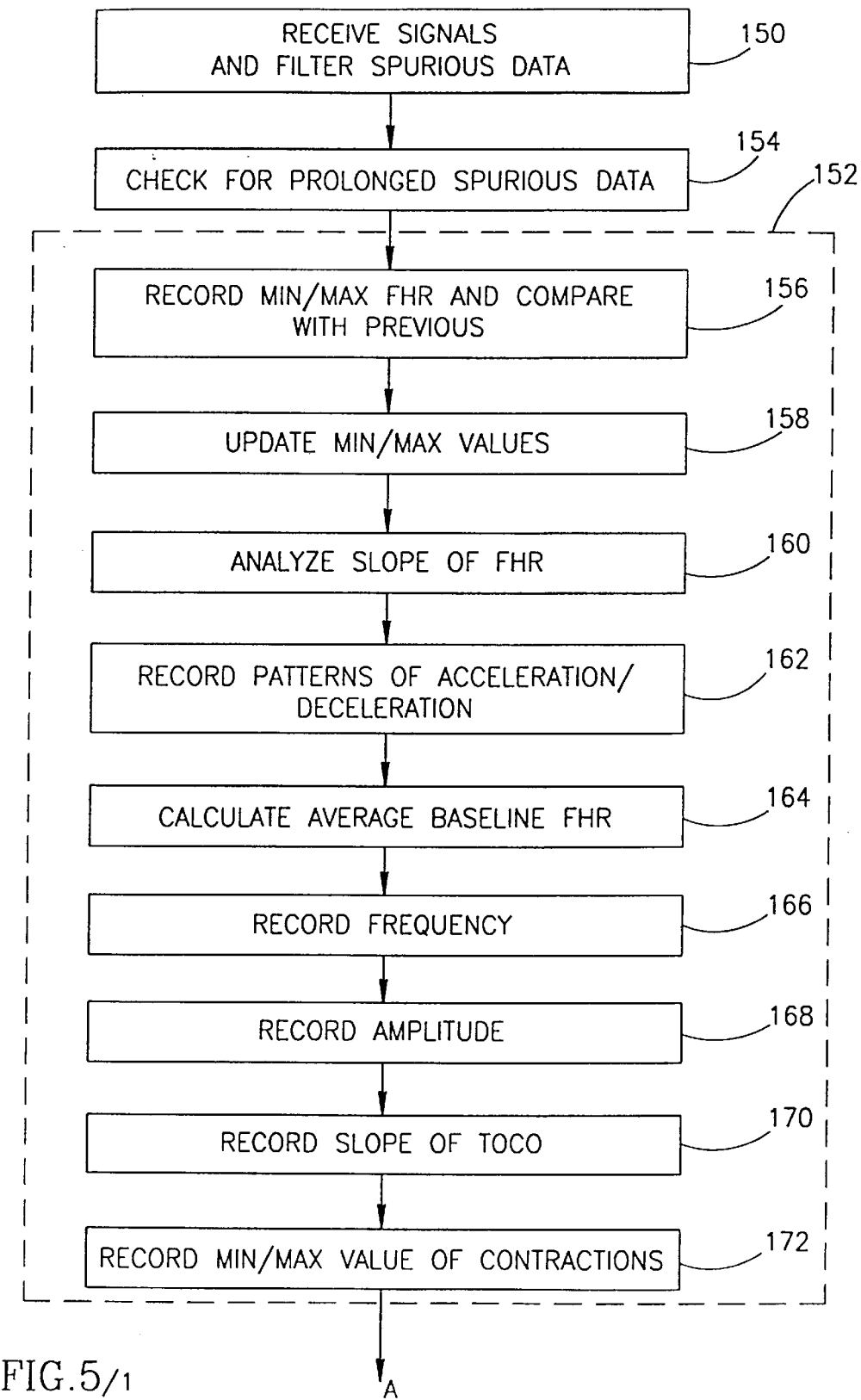
FIG.5/1

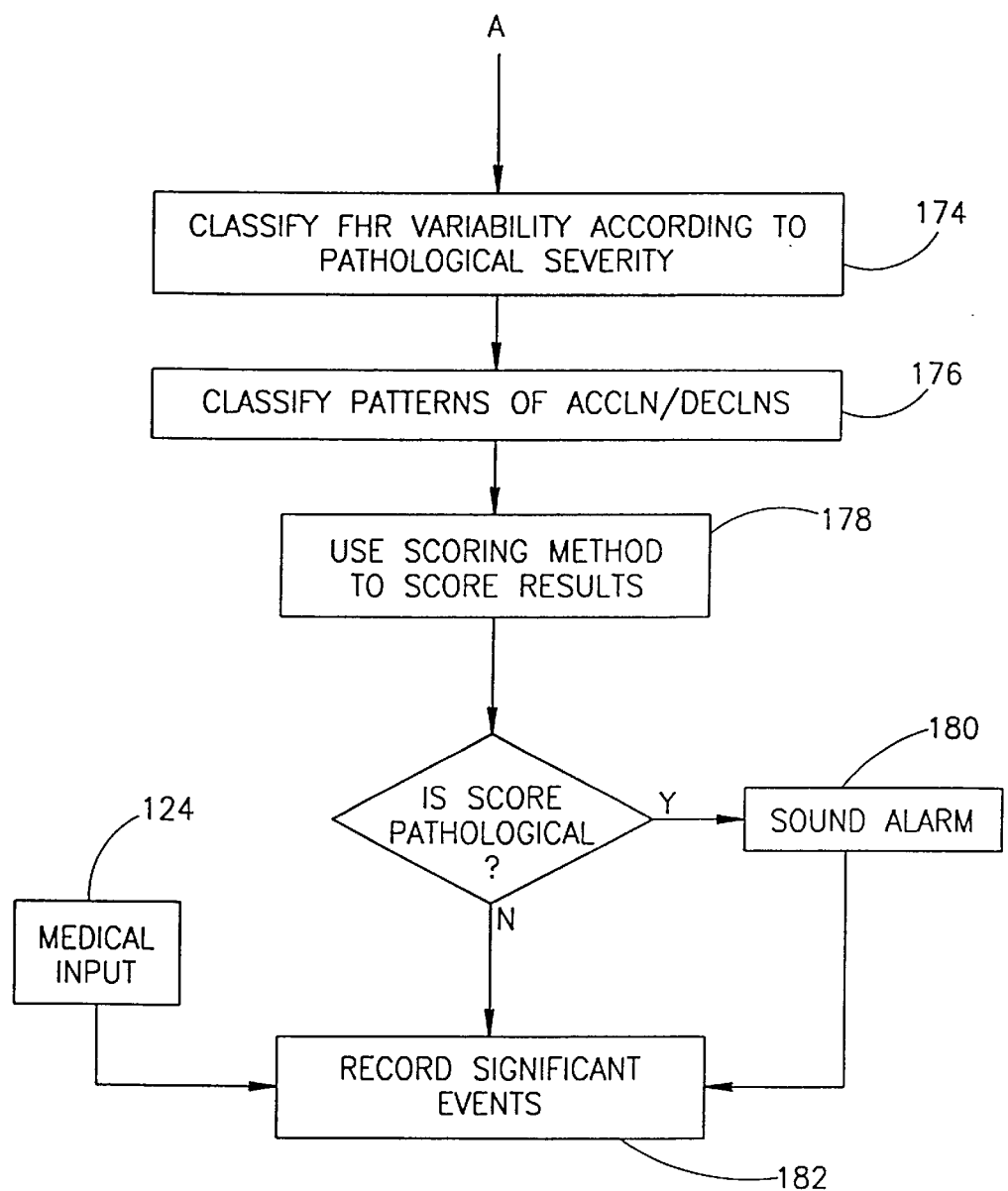
FIG.5/2

FETAL MONITORING SYSTEM AND METHOD

FIELD OF THE INVENTION

The present invention relates to the evaluation of the condition of a fetus and more particularly to a system and method for detecting and monitoring the condition of a fetus prior to and during birth.

BACKGROUND OF THE INVENTION

In gynecology and obstetrics, the simultaneous assessment of the fetal heart rate (FHR) and uterus activity (TOCO) are usually the main parameters used to determine the fetal condition. Monitors, known as fetal monitors or cardiotocographs (CTG monitors) are used for measuring and recording both these parameters.

Establishing a diagnosis on the basis of information provided by the CTG, is a critical and sensitive process. The fetal heart rate trace, for example, may contain a multiplicity of different patterns. The diagnostic meaning of these patterns depends on their frequency and their spectral components, that is, a certain pattern in a given range may have another meaning if it appears in another spectral range. The interrelation between the FHR trace and the TOCO channel and the degree of events is also significant for correctly diagnosing a fetal condition. The assessment of the CTG is very sensitive to misinterpretation. A false or incomplete diagnosis may seriously endanger the fetus and/or the mother.

In order to prevent against the serious consequences of CTG misinterpretation, there have been several attempts to "formalize" the process of CTG interpretation. So-called "score tables" list several criteria or patterns which may appear in the CTG and assign a "score" or "points" (usually, an integer or a natural number) to listed criteria or patterns. By addition of the single scores, one obtains a "sum-score". A reference table relates the "sum-score" directly to the diagnostic assessment. For example, in one system which scores within a range of 0–25 with higher scores indicating progressively more critical situations, a sum-score equal to or exceeding 10 may be classified as "pathologic", indicating high danger for the fetus. A sum-score equal to or exceeding 6 may be classified as "prepathologic", indicating that increased attention is necessary and a sum-score below 4 is classed as "normal".

There have already been attempts in the prior art to automate the process of CTG scoring. However, none of these systems has proven particularly successful. CTG interpretation systems already available on the market are restricted to the calculation of the fetal heart rate variability, special indices or factory-defined scores. The calculated variability, indices and scores do not match the well-known score tables hitherto used for manual CTG evaluation.

U.S. Pat. No. 5,442,940 to Secker et al. describes apparatus and a method for evaluating a fetal condition which allows the individual physician to "edit" and "modify" the rules controlling the operation of the apparatus. Allowing the physician to change the rules, does not allow for a consistent set of rules. Though the above method indicates an alarm situation, it does not specify the reasons causing the alarm. Further, though Secker indicates a net "score", he does not detail the breakdown and computation for this score.

The Sonicaid System 8000 manufactured by Oxford Sonicaid Ltd. of West Sussex. England is a stand-alone system for monitoring the fetal condition of the at-risk pregnancy. The system analyzes key CTG parameters and displays a graph and recordings of up to one hours data. The system does not continuously record and is limited to recording one fetal sensor at a time.

None of the prior art systems permit the simultaneous connection of a plurality of fetal monitors nor do they allow for the connection of any type of fetal monitor, regardless of manufacture.

SUMMARY OF THE PRESENT INVENTION

It is an object of the present invention to provide a fetal monitoring system which overcomes the limitations and disadvantages of prior art systems.

It is a further object of the present invention to provide a fetal monitoring system which allows for the simultaneous monitoring of more than one fetal monitor.

It is a yet further object of the present invention to provide a fetal monitoring system for the connection of a plurality of fetal monitors from different manufacturers.

It is a further object of the present invention to provide a method for continuously monitoring a fetus prior to and during labor.

It is a yet further object of the present invention to provide a method for detecting fetal distress.

There is therefore provided, in accordance with a preferred embodiment of the present invention, a system for monitoring the condition of at least one fetus which includes a plurality of fetal well-being sensors, each of which detects signals during a monitoring period. The system also includes at least one interface unit, a central processing unit connected to the interface unit and a monitoring unit connected to the central processing unit. The interface unit is connected to each of the fetal well-being sensors and includes transmitting means for transmitting the detected signals. The central processing unit includes means for receiving and processing the signals. The monitoring unit enables the medical staff to monitor the transmitted and processed signals.

Additionally, there is provided, in accordance with a preferred embodiment of the present invention, a system for monitoring signals detected from at least one fetal well-being sensor. The system includes at least one interface unit connected to each of the fetal well-being sensors for transmitting the detected signals, a central processing unit connectable to each of the interface units, the central processing unit receiving the transmitted signals and including means for processing the transmitted signals, and a monitoring unit connectable to the central processing unit for enabling medical staff to monitor the transmitted and the processed signals.

Furthermore, in accordance with a preferred embodiment of the present invention, the interface unit includes a signal processor for processing the detected signals.

Furthermore, in accordance with a preferred embodiment of the present invention, the detected signals include data including at least the fetal heart rate of the fetus and/or uterine contractions.

Furthermore, in accordance with a preferred embodiment of the present invention, the monitoring unit includes a display unit for displaying the transmitted and processed data, and an input unit for interactively communicating with the central processing unit.

Furthermore, in accordance with a preferred embodiment of the present invention, the system further includes storage means coupled to the central processing unit for storing the transmitted and processed data.

Furthermore, in accordance with a preferred embodiment of the present invention, the system further includes an archive unit connected to the central processing unit. The archive unit has means for archiving and storing the transmitted and processed data.

Furthermore, in accordance with a preferred embodiment of the present invention, the system further includes a remote monitoring unit connected to the archive unit.

Furthermore, in accordance with a preferred embodiment of the present invention, the remote monitoring unit includes a display unit and an input unit.

Furthermore, in accordance with a preferred embodiment of the present invention, the system further includes a modem connected to the central processing unit. The modem includes means for the transmission of the transmitted and processed signals.

Furthermore, in accordance with a preferred embodiment of the present invention, the system further includes a modem communicator unit for receiving the modem transmitted signals.

Furthermore, in accordance with a preferred embodiment of the present invention, the central processing unit further includes coordinating means for identifying, coordinating and communicating with the fetal well-being sensor.

Furthermore, in accordance with a preferred embodiment of the present invention, the system further includes an individual adapter connected to each of the fetal well-being sensors and an individual display unit connected to each of the individual adapters.

Furthermore, in accordance with a preferred embodiment of the present invention, the system further includes a processing unit connected to each of the individual adapters and a modem communicator unit connected to the processing unit for receiving transmitted signals from the central processing unit.

In addition, there is also provided, in accordance with a preferred embodiment of the present invention, a method for monitoring the condition of at least one fetus. The method includes the steps of:

a) detecting signals regarding the state of each of the fetuses;

b) transmitting the detected signals data;

c) processing the transmitted data; and d) displaying the transmitted and processed data.

Furthermore, in accordance with a preferred embodiment of the present invention, the step of detecting includes detecting at least the fetal heart rate of the fetus and/or uterine contractions.

Furthermore, in accordance with a preferred embodiment of the present invention, the step of detecting further includes detecting the relative time of the detected fetal heart rate signals and the relative time of the detected uterine contractions signals.

Furthermore, in accordance with a preferred embodiment of the present invention, the method further includes the step of inputting data.

Furthermore, in accordance with a preferred embodiment of the present invention, the step of processing includes the steps of:

a) processing the transmitted signals;

b) comparing patterns of the transmitted signals from a database of patterns;

c) correlating the fetal heart rate pattern and the uterine contraction pattern;

d) assigning a numerical value to the correlation; and e) diagnosing the condition of the at least one fetus.

The steps of processing, comparing, correlating, assigning and diagnosing are undertaken in accordance with pre-determined parameters.

Furthermore, in accordance with a preferred embodiment of the present invention, the step of processing further includes the step of processing the input data.

Furthermore, in accordance with a preferred embodiment of the present invention, a plurality of transmitted data is processed together within at least one pre-determined time period.

Furthermore, in accordance with a preferred embodiment of the present invention, the step of displaying any or all of the following:

a) displaying a trace of the fetal heart rate pattern;

b) displaying a trace of the uterine contraction pattern;

c) displaying a description of the correlated patterns;

d) displaying an indication of the assigned numerical value;

e) displaying an indication of the diagnosis.

Furthermore, in accordance with a preferred embodiment of the present invention, the step of processing includes any or all of the following steps:

a) analyzing and identifying accelerations and decelerations in the fetal heart rate pattern;

b) calculating the average of the fetal heart rate within a pre-determined time period;

c) analyzing the pattern of uterine contractions;

d) indicating an alarm whenever the diagnosed condition of the at least one fetus exceeds pre-determined parameters, thereby indicating an alarm situation.

Furthermore, in accordance with a preferred embodiment of the present invention, the method further includes the step of storing the transmitted processed data signals.

Furthermore, in accordance with a preferred embodiment of the present invention, the method further includes the step of archiving the transmitted and processed data signals.

Furthermore, in accordance with a preferred embodiment of the present invention, the method further includes the step of archiving the transmitted and processed data signals.

Furthermore, in accordance with a preferred embodiment of the present invention, the method further includes the step of displaying the archived data signals.

Furthermore, in accordance with a preferred embodiment of the present invention, the method further includes the step of recalling any of the transmitted and processed data and displaying the recalled data signals.

Furthermore, in accordance with a preferred embodiment of the present invention, the method further includes the step of transmitting the transmitted and processed data signals to a remote receiving unit.

Furthermore, in accordance with a preferred embodiment of the present invention, the step of indicating an alarm further includes the step of displaying the alarm indications in order of severity.

Additionally, there is provided, in accordance with a preferred embodiment of the present invention, a system for monitoring signals detected from at least one fetal well-being sensor. The system includes an interface unit connected to each of the fetal well-being sensors for transmitting the detected signals; a local processing unit connectable to the interface unit, the local processing unit receiving the transmitted signals and including means for processing the transmitted signals, and a local monitoring/display unit connectable to the local processing unit for enabling medical staff to monitor and for displaying the transmitted and the processed signals.

Furthermore, in accordance with a preferred embodiment of the present invention, the detected signals include data from the fetal heart rate of the fetus and/or uterine contractions.

Furthermore, in accordance with a preferred embodiment of the present invention, the system further includes an archive unit, coupled to the local fetal monitoring system, the archive unit having means for receiving, archiving and storing the transmitted and the processed signals from each of the local fetal monitoring systems.

Furthermore, in accordance with a preferred embodiment of the present invention, the local monitoring/display unit includes an input unit for interactively communicating with the archive unit and the local processing unit, and/or storage means coupled to the local monitoring/display unit for storing the transmitted and processed signals.

Furthermore, in accordance with a preferred embodiment of the present invention, the system further includes a main processing unit connectable to each of the local fetal monitoring systems, the main processing unit including means for receiving and processing signals from each of the local fetal monitoring systems. The main processing unit is connected to the archive unit.

Furthermore, in accordance with a preferred embodiment of the present invention, the system further includes at least one remote monitoring unit connected to the archive unit. The remote monitoring unit includes a display unit and an input unit.

In addition, in accordance with a preferred embodiment of the present invention, the system also includes a modem coupled to the local processing unit and a modem communicator unit coupled to the main processing unit for identifying, coordinating and communicating with the at least one local fetal monitoring system.

BRIEF DESCRIPTION OF THE DRAWINGS

The present invention will be understood and appreciated more fully from the following detailed description taken in conjunction with the drawings in which:

FIGS. 4A and 4B are graphical illustrations of the fetal heart rate (FHR) and uterine contractions (TOCO) data, respectively;

FIGS. 5/1 and 5/2 are a detailed flow chart illustration of the operation of processing the transmitted data;

DETAILED DESCRIPTION OF A PREFERRED EMBODIMENT

Figure 1:
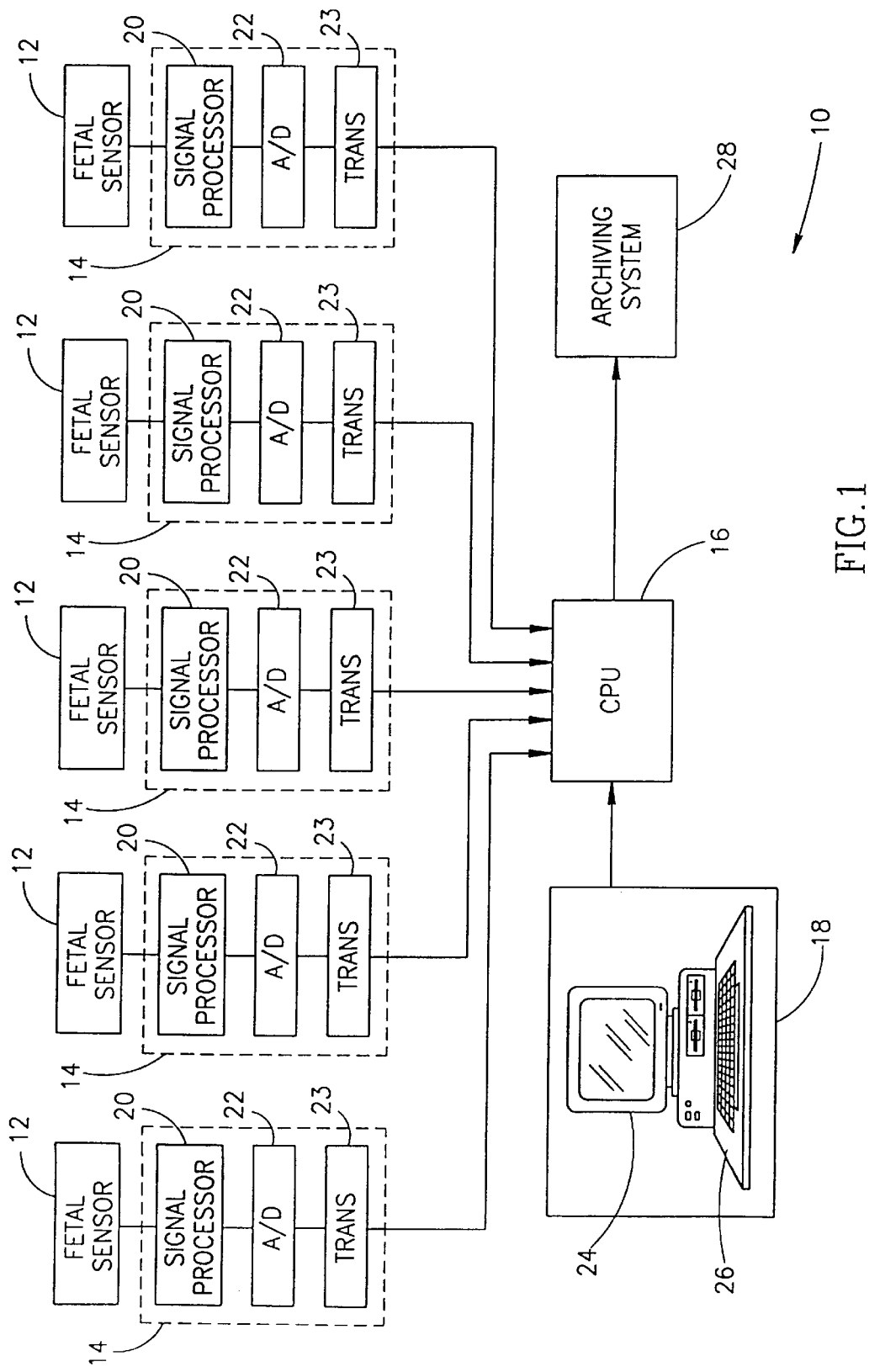
FIG. 1, is a schematic illustration of a fetal monitoring system constructed and operative in accordance with a preferred embodiment of the invention.

Reference is now made to FIG. 1, which schematically illustrates a fetal monitoring system, generally designated 10, constructed and operative in accordance with a preferred embodiment of the invention. The fetal monitoring system 10 comprises at least one fetal well-being sensor 12 connected via an interface unit 14 to a central processing unit 16. The central processing unit 16 filters, processes and analyzes the data received from each of the fetal monitors 12. The condition of the fetus being monitored is indicated on a centrally located monitoring station 18, which is preferably connected to the central processing unit 16.

For the purposes of example only, FIG. 1 illustrates a delivery ward having five patients, to each of whom a fetal well-being sensor 12 is connected. It is a feature of the invention that any known in the art fetal well-being sensor 12 may be used, irrespective of manufacturer, and, if desired, a combination of different fetal monitors 12 may be used. Each fetal well-being sensor 12 is connected via its own interface unit 14 to the central processing unit 16.

Interface unit 14 comprises a signal processor 20 and an A/D (analog/digital) interface 22 and a transmitter 23. A/D interface 22 connects the signal processor 20 to the transmitter 23.

Each fetal well-being sensor 12 (or CTG (cardiotocograph) monitor) continuously transmits data regarding the fetal heart rate (FHR) and uterus activity (TOCO) of the fetal condition in real time. Time is an essential factor in the analysis and identification of CTG patterns, as will be described in greater detail hereinbelow.

Each fetal well-being sensor 12 is connected to its own interface unit 14. The analog signals received from the fetal well-being sensor 12 are filtered by signal processor 20 to remove any noise form the signals. The A/D interface 22 converts the analog signals into digital data and transfers the digital signals to central processing unit 16. Each of connected fetal monitors 12 is unique and identified according to the bed unit, for example.

Signal processor 20 is any suitable signal processor for filtering spurious noise to extract the data from the signals emanating from the fetal sensor 12.

In an alternative embodiment, signal processor 20 may be replaced by a fetal monitoring device, such as Model 8040 or Model 1351 manufactured by Hewlett Packard of Palo Alto, Calif., USA or the Model 116 manufactured by Corometrics of Connecticut, USA. These commercially available fetal monitoring devices are commonly connected to a fetal sensor for recording the fetal heart rate and TOCO time traces onto a paper strip-chart. These fetal monitoring devices generally carry out pre-processing of the signal and this element of the device may be utilized. Thus, the present invention may be utilized together with and in addition to previously installed fetal monitoring devices.

A/D interface 22 is any known in the art A/D interface for converting the analog signals received from the fetal well-being sensor 12 into digital data. Transmitter 23 is any suitable transmitting device for transmitting the signals detected by the fetal well-being sensor 12.

Central processing unit 16, which receives the digitized data from each of the fetal well-being sensors 12, is any known in the art processor. Each of the fetal well-being sensors 12 is coordinated to communicate with the central processing unit 16 in set sequence and identify themselves according to their bed number. Preferably, a storage medium, of a type known in the art, such as a hard disk or optical drive, is coupled to the central processing unit 16 to store data.

Monitoring station 18 is preferably a known computer-like interface, such as a PC (personal computer) or workstation and preferably comprises at least a standard display screen 24 and a data input device 26. The data input device 26 is any known in the art device such as a standard keyboard. The data input device 26 can be modified to suit the requirements of the monitoring system 10. The use of a central monitoring station 18 allows the medical staff, midwife or physician to supervise a plurality of "beds" in a maternity ward.

Preferably, fetal monitoring system 10 further comprises an archiving unit 28 connected to central processing unit 16. Archiving unit 28 is any suitable storage and archiving system for maintaining a relational and accessible database containing a multitude of records. Any or all the data being processed by central processing unit 16 is archived and stored in archiving unit 28 for later retrieval. Thus, complete previous records for a particular patient can be accessed by the physician, who can utilize the data for comparison and diagnostic purposes.

It will be appreciated by persons skilled in the art that a single display unit 24 is not limited to displaying data from a single fetal well-being sensor 12, but can simultaneously display information from a plurality of fetal sensors 12.

The method of screen display of the medical status of the processed CTG can be any suitable method, known in the art , such as by color coding "score" and messages which provide an immediate at-a-glance summary of the fetal condition.

All the transmitted and input data which is being continually processed by central processing unit 16 is stored in a suitable storage device (not shown) known in the art. The data is constantly accessible by the physician or other supervising attendant. Thus, the physician can request a "playback" of the CTG trace or any other data, for example, in order to obtain a long term view of a particular fetus.

After birth and on completion of the monitoring of a specific fetus and mother, the relevant data is downloaded to archiving unit 28 for storage and archiving. Data may also be downloaded during monitoring in order to provide a backup of data in case of a power loss.

Figure 2A:
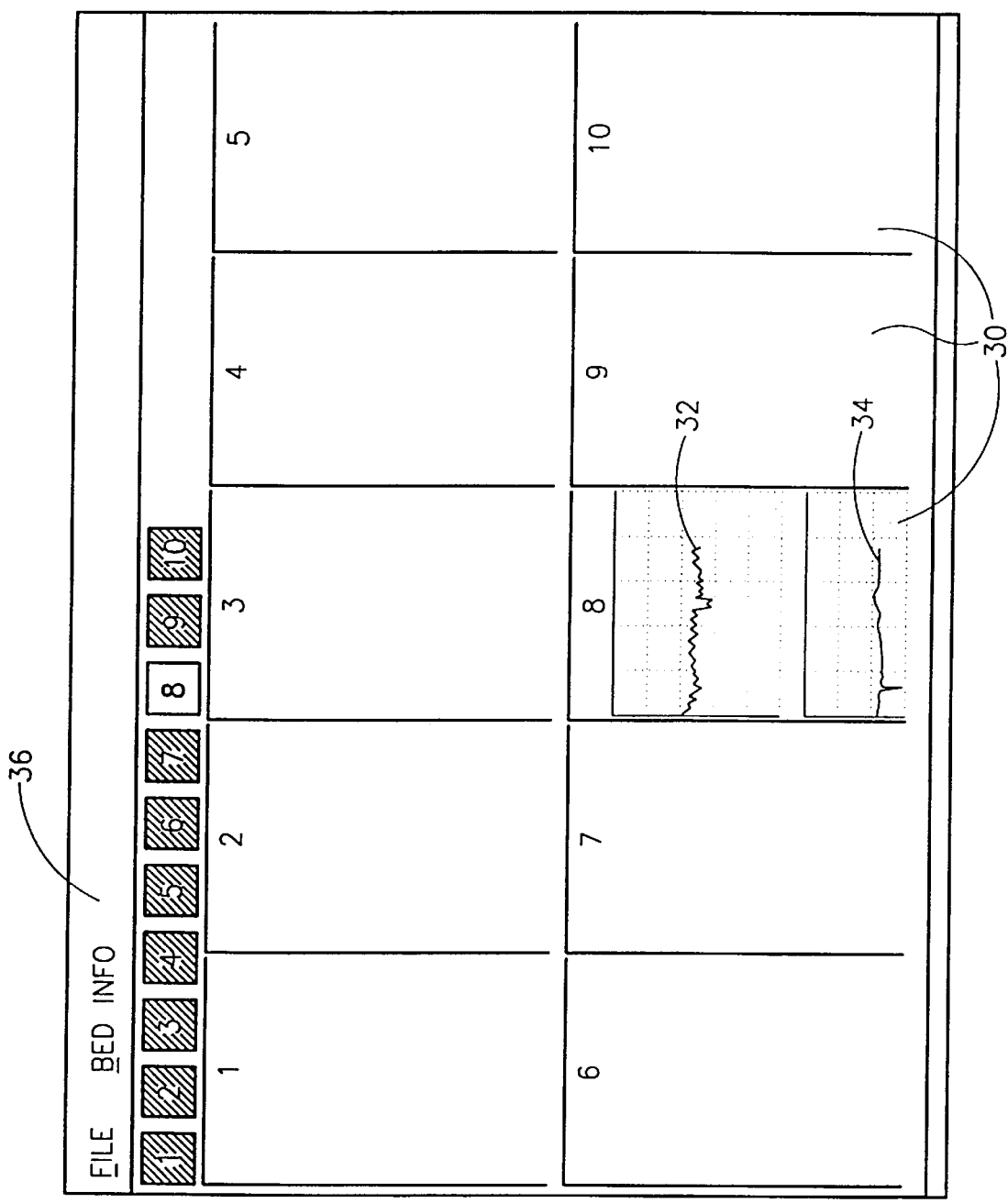
FIGS. 2A, 2B, 2C and 2D are illustrations of alternative screen displays for the fetal monitoring system of FIG. 1.
Figure 2B:
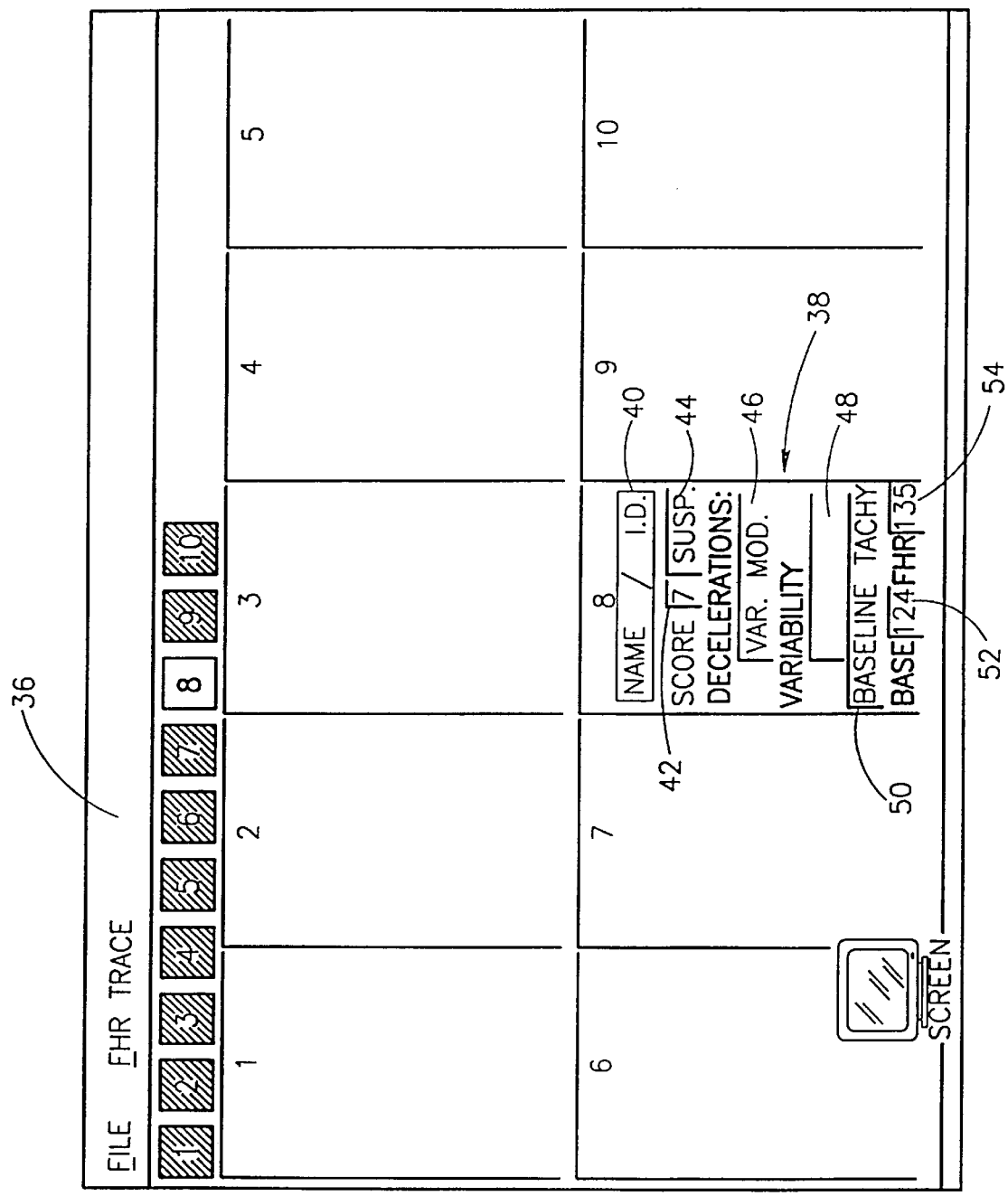

Reference is now made to FIGS. 2A–2D which are illustrative examples of alternative "screens" which may be displayed on the standard display screen 24 of the monitoring station 18. FIGS. 2A and 2B illustrate a screen display having a plurality of windows, generally designated 30 and individually referenced 1 to 10, are illustrated. Each window refers to an individual "bed" and thus FIGS. 2A and 2B illustrate a fetal monitoring system 10 having up to ten fetal monitors 12 attached thereto. Window 8 of FIG. 2A displays a trace of the FHR and TOCO data, 32 and 34, respectively, transmitted over a period of time (x-axis) from bed number 8. The FHR and TOCO traces, 32 and 34, respectively, will be described in greater detail hereinbelow.

Figure 2C:
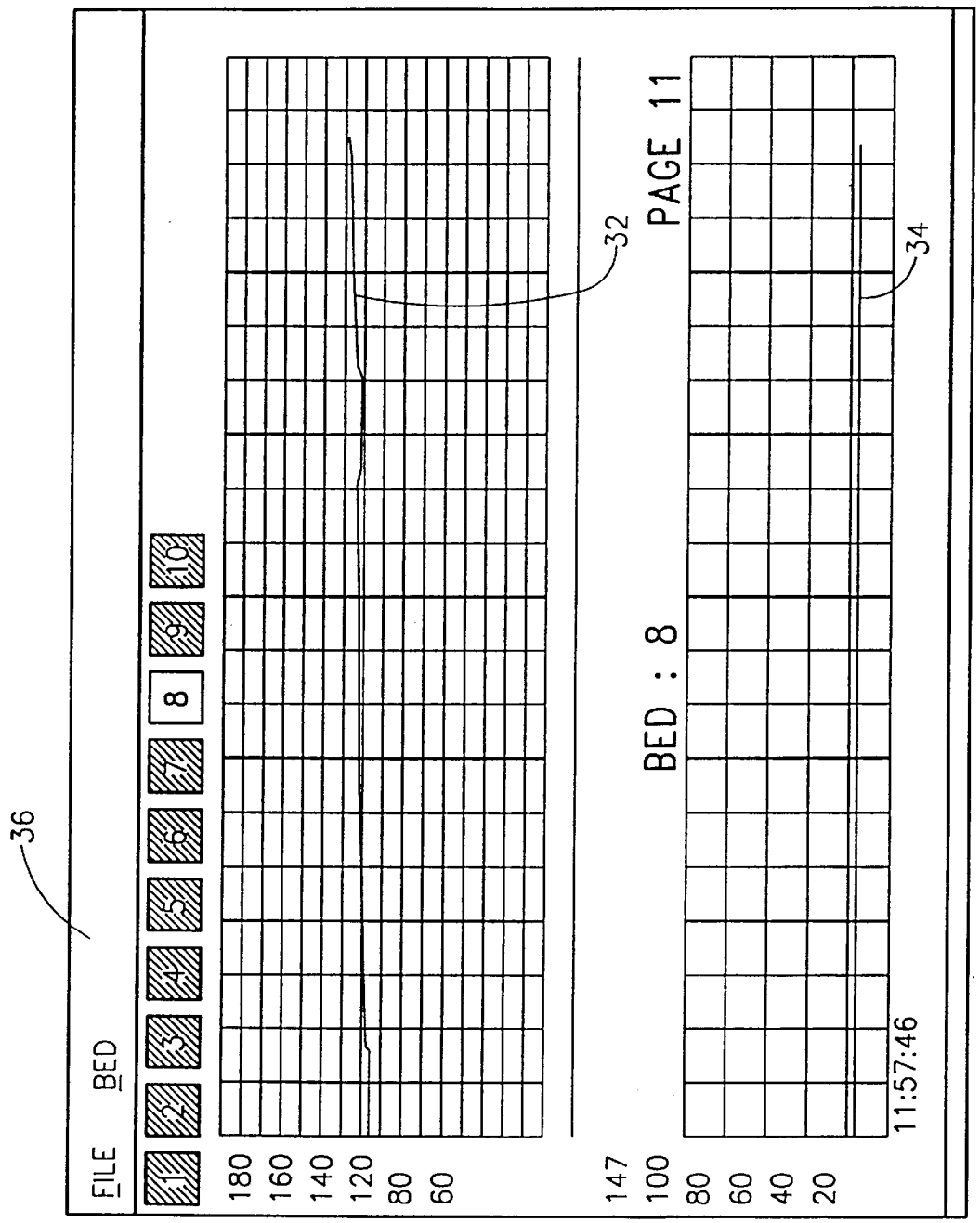
Figure 2D:
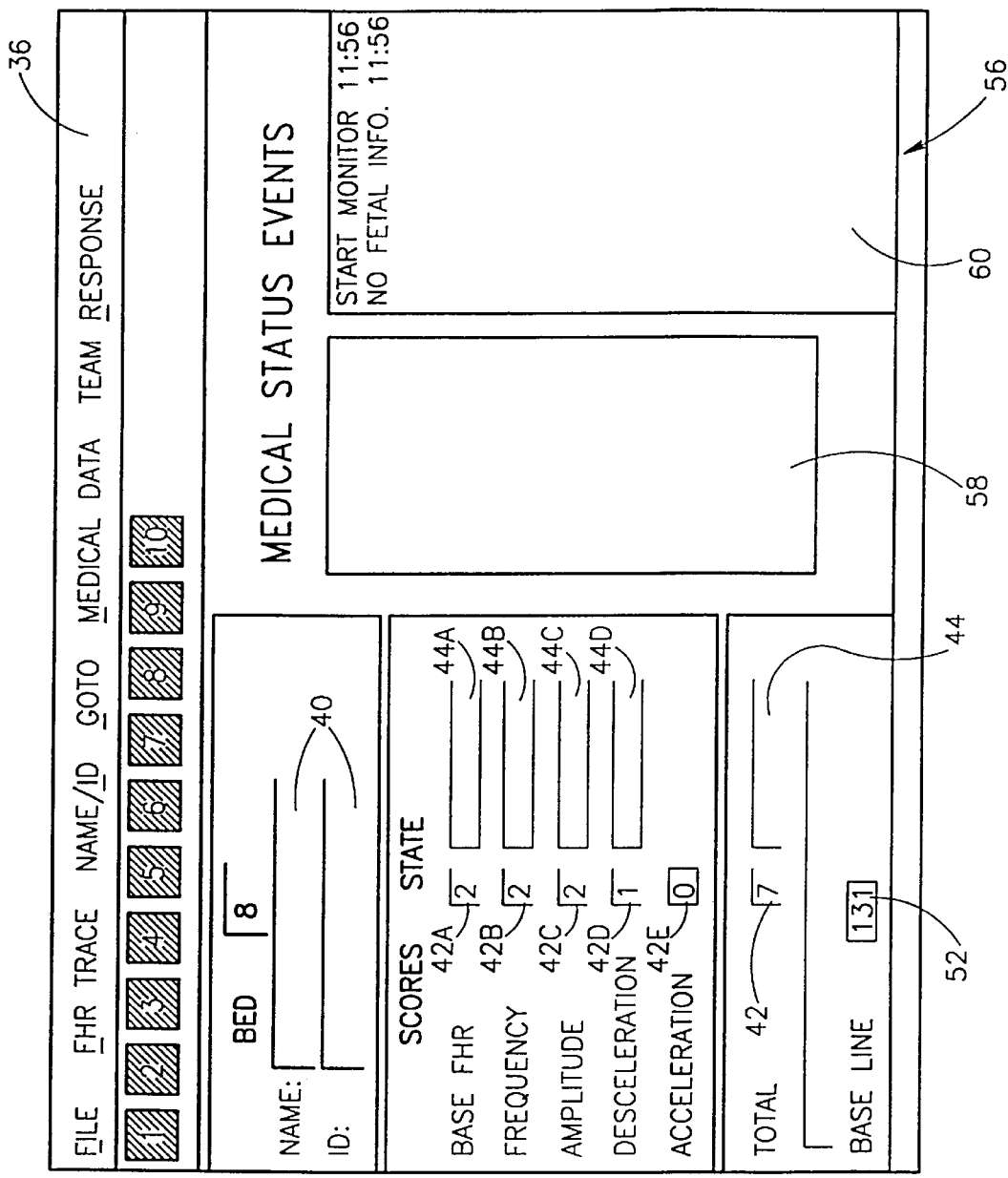

Window 8 of FIG. 2B displays the present the medical data and indicates the "status" of bed 8 in descriptive format. FIGS. 2C and 2D are full screen displays (zooms) of the FHR and TOCO trace and "status" of bed 8, respectively. All the screen displays are interlinked and are accessible via a menu bar 36 indicating the various choices available.

FIG. 2B displays the medical data, generally designated 38, for each of the "beds" linked to the fetal monitoring system 10. For the purposes of example only, the medical data 38 displayed includes the name and identity of the patient 40, the total score 42, a descriptive label for the score 44, description of the type of deceleration 46, the variability 48, a description of the present condition 50, the value of the baseline FHR 52 and the current FHR 54.

FIG. 2C is a zoomed full screen display of a particular "bed", showing the FHR and TOCO trace, 32 and 34, respectively. FIG. 2D is zoomed full screen display 56 of the medical data for bed 8. The full screen allows for the display of additional information and the further details related to the data display of FIG. 2A. By way of example only, the full screen display 56 includes similar details to FIG. 2B including the name and identity of the patient 40, the total score 42, a descriptive label for score 44, description of the type of deceleration 46, a description of the present condition 50 and the value of the baseline FHR 52.

Additionally, full screen display 56 also includes a breakdown with description, if appropriate, of the total score 42. Any suitable scoring method, such as the "KREBS" scoring system may be used. The "KREBS" scoring system is described in a paper entitled "Intrapartum Fetal Heart Rate Monitoring"; Part II "Multifactorial Analysis of Intrapartum Fetal Heart Tracings" by Messrs. Krebs H. B., Petres R. G. et al., published in the *Journal of Obstetrics and Gynaecoloqy* 133:773 1979.

The "KREBS" scoring system generally allocates a score between 0 (low) and 2 (high) to each of five variables; the base FHR, the frequency and amplitude of the variability, the deceleration and acceleration, referenced 42a, 42b, 42c, 42d and 42e. In the example of FIGS. 2B and 2D, score 42 totals 7 based on a summation of 2 (base FHR)+2 (frequency)+2 (amplitude)+1 (deceleration)+0 (acceleration). Descriptive labels (44a–44d) corresponding to each of variables 42a–42d may be displayed in adjacent boxes.

The full screen display 56 of FIG. 2D further includes medical events and status windows 58 and 60, respectively, which may be used to display present and historical information, for example, relating to the medical condition of the patient, administered medication and to any relevant events, such as the lack of fetal information for a specific time, beginning of stage II labor or a series of prolonged decelerations.

Figure 3:
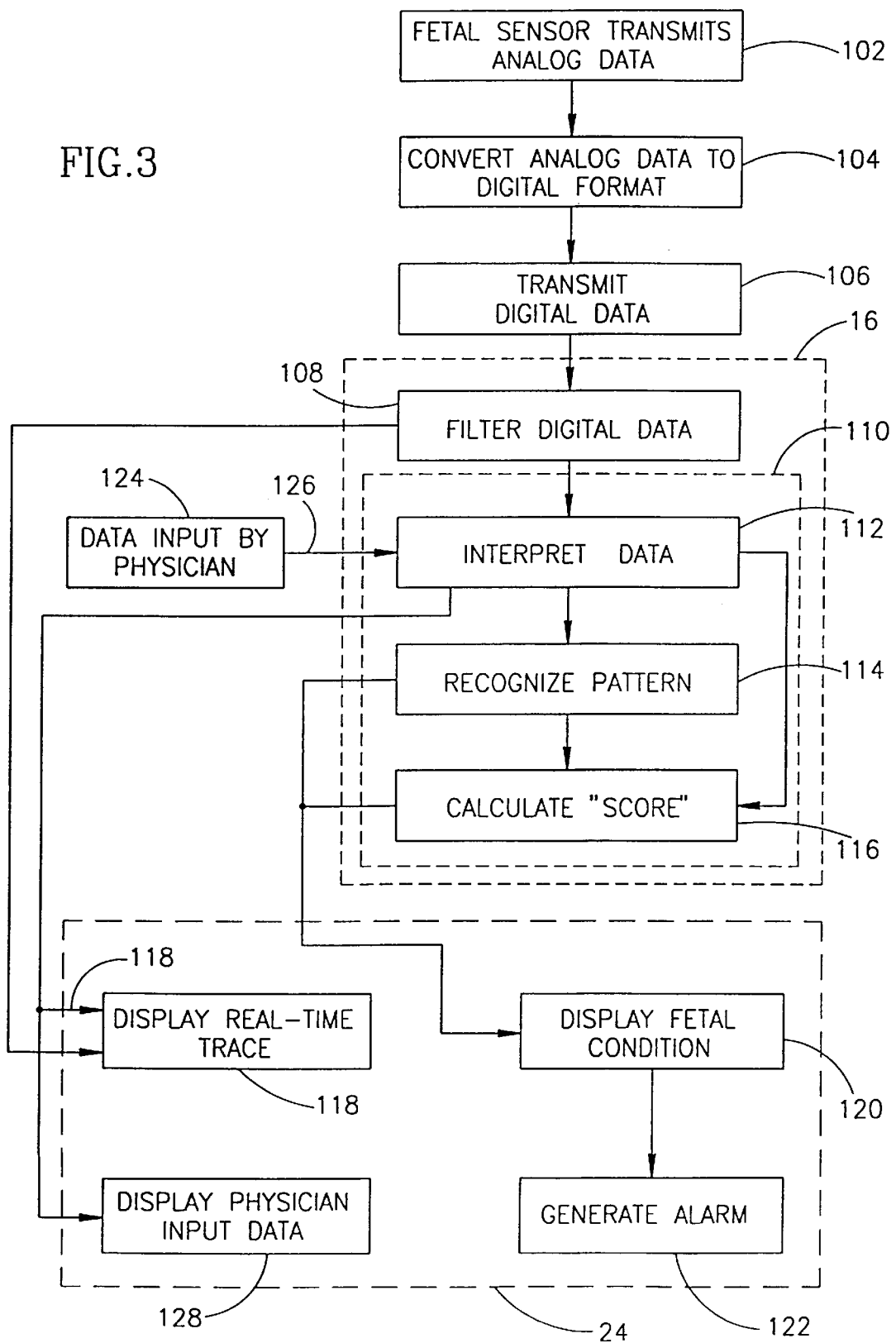
FIG. 3 is a flow chart illustration of the operation of the fetal monitoring system of FIG. 1.

Reference is now made to FIG. 3 which is a flow chart illustration of the operation of the fetal monitoring system 10. Each fetal well-being sensor 12 continuously transmits analog data (step 102) via the interface unit 14 to central processing unit 16. The transmitted data, generally designated 30, comprises at least three data elements, concerning the fetal condition, the FHR (fetal heart rate), the TOCO (uterus activity) and additionally, the real time (referenced T). The signal is first processed by signal processor 20. The analog data 30 is converted via A/D interface 22 into digital data (step 104). The digital data is then transmitted (step 106) to central processing unit 16, where it is further filtered (step 108). Filtration includes the exclusion of spurious noise and the discarding of any transmission when there is a loss of FHR and TOCO data.

The filtered data is then simultaneously displayed on a suitable display 24 and processed (step 110) by central processing unit 16. The processing step (110) includes the step of processing the data (step 112), "recognizing", or comparing and correlating patterns, (step 114) and assigning a "score" (step 116). The TOCO pattern can be displayed (step 118) on screen display 24 in real time in the form of a CTG trace.

The combination of "patterns" and the "score" indicate the condition of the fetus, enabling a diagnosis to be made. The analysis of the transmitted data, including the "pattern" and the "score" (fetal condition ) can be displayed separately or together (steps 118 and 120, respectively). Should the fetal condition be pre-pathologic or pathologic, an alarm is generated (step 122).

A pre-pathologic condition generally indicates that increased attention is due and a pathologic condition generally indicates that the fetus in potential danger. The generated alarm (step 122) can be indicated in any suitable visual or audio manner. Preferably, both visual and audio signals can be generated.

The processing steps (110–122) will be described in greater detail hereinbelow.

The medical condition of the mother and fetus is not exclusively determined by the data transmitted from the fetal well-being sensor 12, but also includes other factors such as the type and quantity of medication prescribed and the general health of the mother. Additional data concerning medication, for example, can be input by the physician (step 124) via any suitable input device such as the keyboard 26, tablet, mouse device or touch screen. The input data is processed (step 126) by central processing unit 16. Any required adjustments are made during processing and the revised "score" displayed (step 120). Preferably, any data input by the physician is also displayed on the screen (step 130) and recorded in the list of events in the archiving unit 28.

Reference is now made to FIGS. 4A, 4B, 5/1 and 5/2. FIGS. 4A and 4B are graphical illustrations (charts) of the fetal heart rate (FHR) and uterine contractions (TOCO), respectively. The upper chart line 70 (FIG. 4A) illustrates the FHR measured in beats per minute (bpm on y-axis) over a period of time (x-axis) and the peaks (72a and 72b) of the lower chart line 74 (FIG. 4B) illustrate contractions during the same time period (x-axis). The hatched section 76 (FIG. 4A) indicates the normal fetal heart range, that is between 120 and 160 bpms. The FHR chart further illustrates primary and secondary accelerations 78a and 78b, respectively as components of a variable deceleration 80. Each time period (between vertical lines 82) are equally spaced. In the example of FIGS. 3 and 4, the time period refers to a time of six seconds.

FIGS. 5/1 and 5/2 is a detailed flow chart illustration of the step of processing the data (step 110, FIG. 2). As described with respect to FIG. 2, the step of processing the data (step 110) comprises the steps of processing the transmitted digital data signals (step 112), recognition of patterns (step 114) and calculating the "score" and CTG diagnosis (step 116).

Data signals of FHR and TOCO are continuously transmitted at a preferred rate of once per second. Spurious data is first filtered out and rejected (step 150). Spurious may be defined as data which is outside pre-determined limits.

For each time period (of six seconds), the latest six sets of data (one set of data for each second) for the FHR and TOCO are processed together (step 152). The time period of six seconds between processing is a preferred period and is used by way of example only, without being in any way limiting to the present invention. A check is made for prolonged spurious data (step 154), which might occur if fetal information is lost. Flat periods indicating the lack of data are discarded without any further processing being carried out.

The checks and calculations, detailed hereinbelow are made for each time period (of six sets of data). For example, a single time period, designated T1, is referred to in the following description:

a) The minimum and maximum fetal heart rates (FHR) are noted (step 156) and compared with the previously recorded and stored minimum and maximum rates (84 and 86, respectively). If the present values are smaller or larger than the stored values, the minimum and maximum rates, 84 and 86 respectively, are updated (step 158). The slope of the FHR (that is the change in the rate) is analyzed (step 160) to identify any acceleration or deceleration in the FHR. The pattern of accelerations or decelerations are also noted (step 162). Different patterns, such as periodic accelerations as components of variable decelerations, illustrated in FIG. 3A, are significant indicators of the fetal condition.

b) The average baseline FHR (line 88) is continuously calculated (step 164) and the values for the frequency (step 166) and amplitude (step 168) of the short-term variability are also updated. The baseline FHR is an average of the FHR, excluding accelerations or decelerations, calculated over a ten-minute period, for example.

c) The presence, peak and duration of contractions are noted from analysis of the TOCO chart (FIG. 3B). The current slope (line 90), maximum and minimum values, 92 and 94, respectively are recorded (step 172).

d) The baseline FHR and variability (recorded in steps 164–168) are then classified according to their pathological severity (step 174).

e) By reference to pre-input classification tables, the pattern of accelerations or decelerations, recorded in step 162, are classified (step 176).

f) A scoring method is used to "score" and describe the current parameters and classifications (step 178). Any suitable scoring method, such as the "Krebs" scoring system described hereinabove may be used.

g) If the results indicate a pathological situation, for example, an "alarm" is triggered and indicated on the screen display 24 (FIG. 1) (step 180). If more than one bed indicates an alarm situation, the alarms are displayed according to an hierarchy of severity. That is, where there are several alarm situations arising at more or less the same time, a more critical alarm situation takes precedence over a lesser alarm situation and is continuously indicated until action is taken by the medical staff. The medical staff has the option of overruling certain alarm situations, such as the incidence of a continuously sounding alarm considered to be "minor".

h) "Significant events" are recorded (step 182). "Significant events" refer to any events which are relevant to the progress of labor, administered medication and medical intervention, such as response to an alarm situation in g. above.

The real-time display and internal timers are updated for each time period.

A feature of the present invention is the use of a consistent scoring and diagnostic evaluation system incorporated within the fetal monitoring system for evaluating the transmitted and input data. Scoring and diagnostic evaluation system is not subject to arbitrary change by a physician or anyone else. In other words, the diagnostic evaluation system is based on identification of known CTG events, and thus is capable of generally evaluating and diagnosing the majority of events. The diagnostic evaluation system is an integral component of the processing carried out by the central processing unit 16. The diagnostic evaluation system is based on processing and analyzing the transmitted and input data.

For the purposes of example only and without in any way being limiting to the present invention, the base FHR, frequency and amplitude of the variability, deceleration and acceleration of the FHR are used by the "KREBS" scoring system to calculate the total score (step 178). Decelerations include their classification relative to the peak contraction time, (that is early, late or variable plus mild, moderate or severe), end-stage decelerations and multiple decelerations.

Additionally, the loss of fetal information, baseline tachycardia and bradycardia, sinusoidal FHR, hypertonus and abnormal multiple contraction rate are examples of criteria which may be used to determine the condition of the fetus, recognize patterns, and for CTG diagnosis.

It will be appreciated by persons knowledgeable in the art that there are a very large number of possible patterns indicative of different types of fetal distress. The system comprises a database of patterns including, for example, but not limited to "patterns" described within the text book *"Fetal Monitoring Interpretation"* by M. L. Cabaniss, published by J. B. Lippincott Company.

Time is an essential factor in the analysis and identification of patterns in the CTG traces. That is, there are factors that must be integrated over time to determine a certain condition. It is a further feature of the present invention that the data is transmitted and processed in "real-time", that is the relationship between the time an event occurs and the event itself are processed and analyzed.

For example, "bradycardia" occurs if FHR<80 bpm for 1 minute. Variability is integrated over a continuously sliding 5 minute window. An alarm for "Chronic FHR Change" is signaled if a score of 7 persists for 45 minutes, a score of 6 persists for 30 minutes, or a score of 5 persists for 10 minutes.

Among types of data which may be input by medical staff and which are taken into account in the analysis of the CTG include, but are not limited to, the administration of Pethidine™, the connection of external or internal FHR monitor, the notification of Stage II labor (that is the latter stages of labor) and the use of epidural anesthesia.

In the event of a prolonged loss of FHR data, the analysis can be temporarily stopped by the medical staff, so as to prevent the system from automatically terminating the record of delivery and closing the patient's record file. The central processing unit 16 is configured to automatically open a file whenever a fetal well-being sensor 12 is connected to the system and also automatically closes the file after delivery and after a pre-determined time of inaction.

Data input by medical staff includes but is not limited to actions taken by the attending medical team during labor and delivery, such as change of position of the laboring woman, the use of oxygen, the giving of Ritodrin™, stopping the Pitocin™ drip, recording fetal pH measurement and recording the method of delivery.

As will be appreciated by persons knowledgeable in the art that the fetal monitoring system 100 may also be used to monitor a perinatal fetus prior to labor. That is, the fetal heart rate of a fetus may be monitored. Fetal monitoring system 100 may be used in conjunction with the "DAWES" method for fitting baselines to fetal heart rates and analyzing the patterns of episodic variations, accelerations and decelerations. The "DAWES" method is described in a paper entitled "Pattern of Normal Fetal Heart Rate"; by Messrs. G. S. Dawes et al., published in the *Journal of Obstetrics and Gynaecoloqy* Vol 89 pp. 276–284, April 1982.

Figure 6:
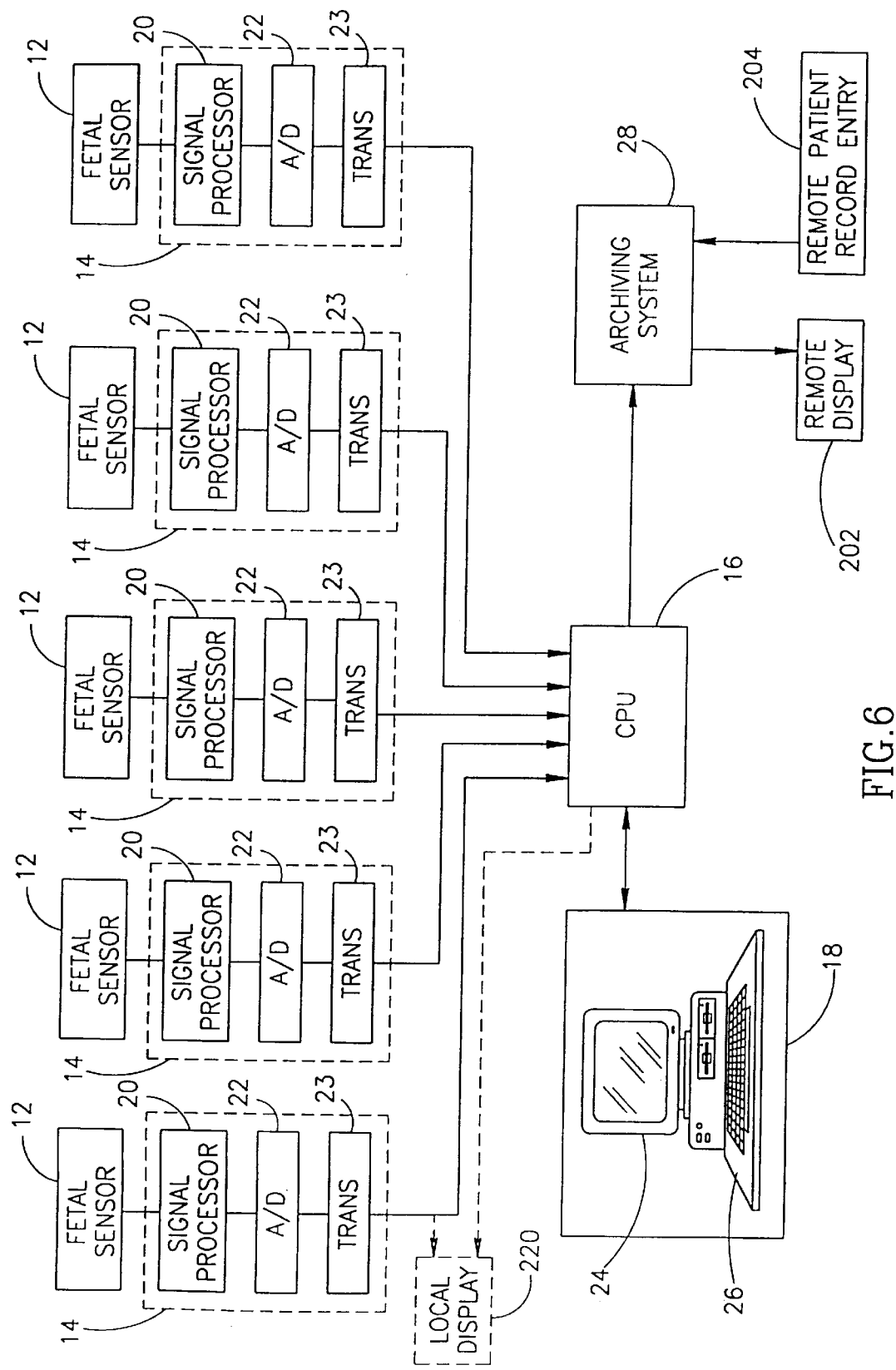
FIG. 6 is a schematic illustration of a further preferred embodiment of a fetal monitoring system.

Reference is now briefly made to FIG. 6 which illustrates a further embodiment of a fetal monitoring system, generally designated 200. The fetal monitoring system 200 contains the similar elements to fetal monitoring system 10 described hereinabove with respect to FIG. 1. Elements of this embodiment of the invention which are similar to elements which have been previously described with respect to the preferred embodiment hereinabove, are similarly designated and will not be further described.

Fetal monitoring system 200 further comprises a remote display unit 202 and a remote input unit 204, suitably connected to archiving unit 28. Remote display unit 202 and remote input unit 204 are known in the art components, similar to display screen 24 and data input device 26, respectively. Remote display unit 202 and remote input unit 204 are located at any convenient location.

The archived traces stored in archive unit 28 can be recalled at any time, using remote input unit 204, and played back. The retrieved output is displayed on remote display unit 202. Previous CTG traces, illustrative of actual events, can be used to simulate the progression of labor, and thus is an ideal aid for the purpose of teaching and training.

Fetal monitoring system 200 can further include a local display unit 220 directly connected to any of the individual interface units 14. The local display unit 220 can receive data from the central processing unit 16 either directly or via a modem unit (not shown) attached thereto.

Figure 7:
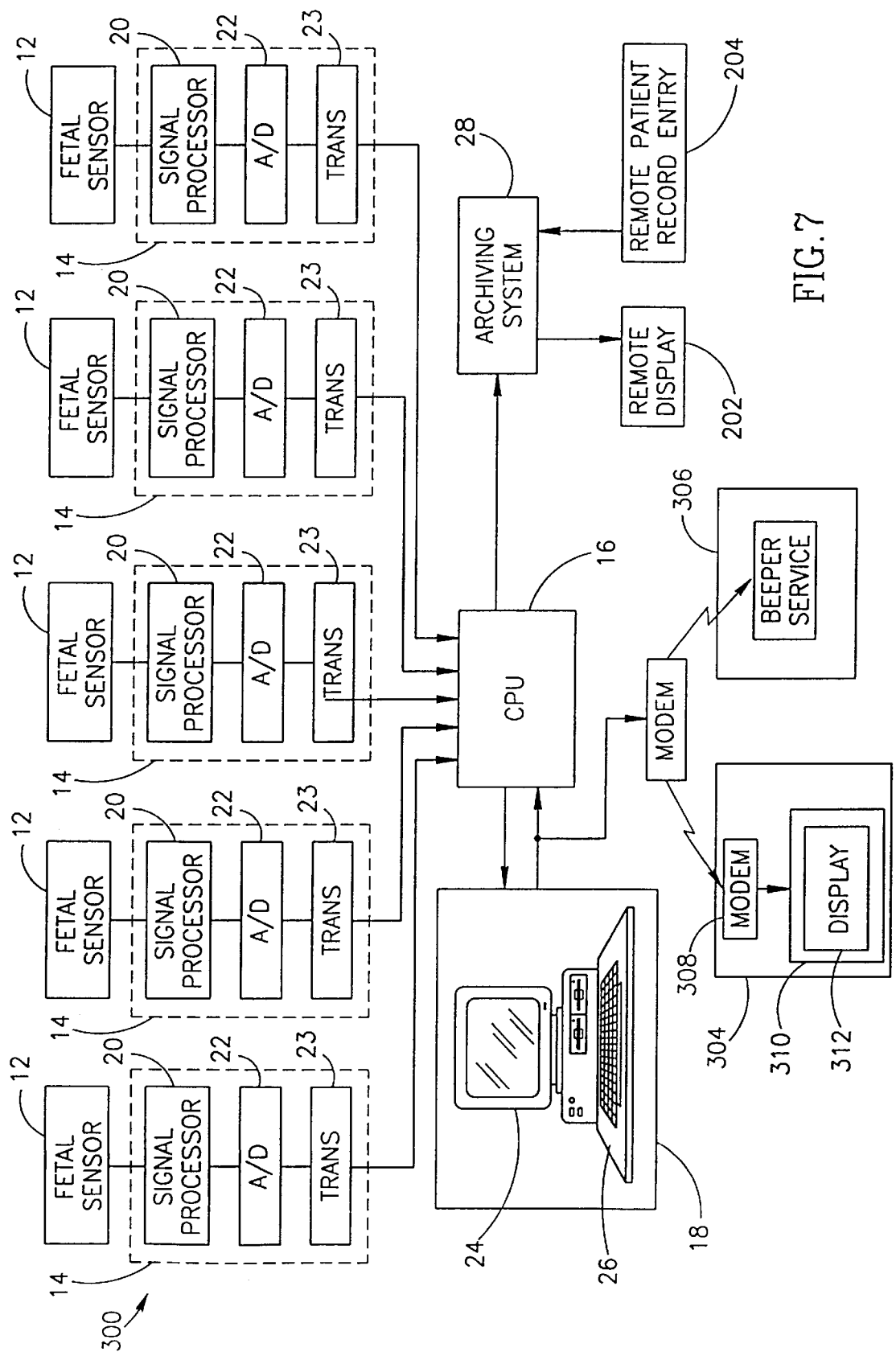
FIG. 7 is a schematic illustration of a further preferred embodiment of a fetal monitoring system.

Reference is now briefly made to FIG. 7 which illustrates a further embodiment of a fetal monitoring system, generally designated 300. The fetal monitoring system 300 contains the same elements as fetal monitoring system 10, described hereinabove with respect to FIG. 1.

Elements of this embodiment of the invention which are similar to elements which have been previously described with respect to the preferred embodiment hereinabove, are similarly designated and will not be further described.

Fetal monitoring system 300 further comprises a modem 302 connected to central processing unit 16. Modem 302 is any suitable known in the art modem (modulator/demodulator) for the transmission of digital data.

Modem 302 can be used to transmit data regarding the condition of a fetus to a remote location, such as a receiving unit 304 or to a paging device 306.

Receiving unit 304 preferably comprises a modem communicator unit 308 connected to the recipients computer system, or similar 310 having a display device 312. Thus, medical staff at a remote location can be notified of any change in the mother or fetus, which generate an "alarm" signal, for example. Medical staff having a computer system can also receive any data related to CTG traces for example, allowing the staff to analyze and diagnose a patient without having to be proximate to the main monitoring unit 18.

Figure 8:
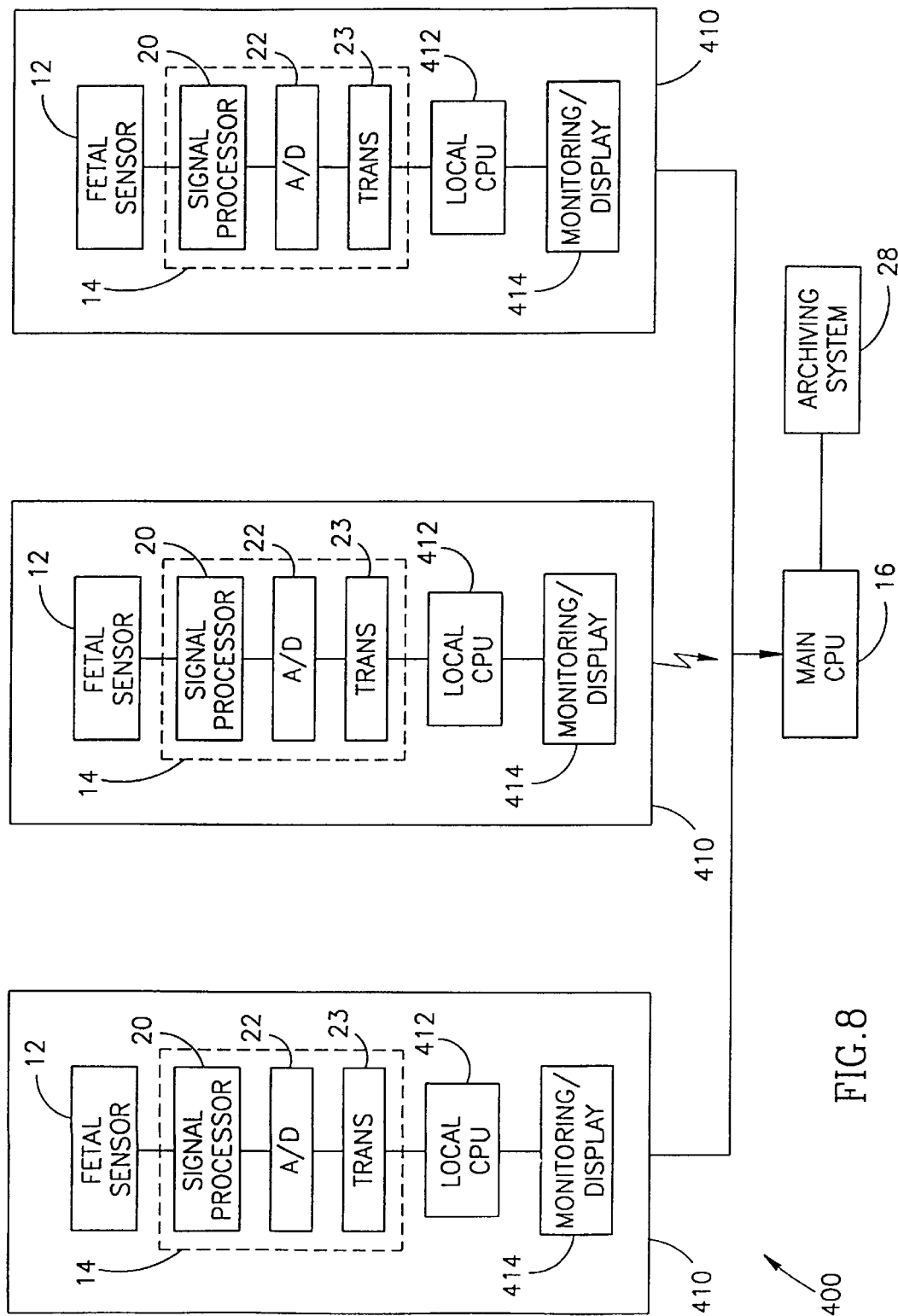
FIG. 8 is a schematic illustration of a further preferred embodiment of a fetal monitoring system.

Reference is now made to FIG. 8 which illustrates a further embodiment of a fetal monitoring system, generally designated 400. The fetal monitoring system 400 contains the similar elements to fetal monitoring system 10 described hereinabove with respect to FIG. 1. Elements of this embodiment of the invention which are similar to elements which have been previously described with respect to the preferred embodiment hereinabove, are similarly designated and will not be further described.

Fetal monitoring system 400 comprises at least one stand-alone, local fetal monitoring system, generally designated 410. Each stand-alone fetal monitoring system 410 comprises a fetal well-being sensor 12 connected via an interface unit 14 to a local processing unit (CPU) 412. A local monitoring/display unit 414 is further coupled to the local CPU 412.

Local CPU 412 and monitoring/display unit 414 are configured so as to be able to carry out similar functions to main CPU 16 and monitoring station 18, respectively, hereinbefore described. That is, local CPU 412 continuously processes data, regarding the fetal heart rate (FHR) and uterus activity (TOCO) of the fetal condition received in real time, from the fetal well-being sensor 12. The received data and/or processed data can be displayed on local display unit 414.

Local monitoring/display unit 414 is preferably a PC (personal computer) or similar workstation and preferably comprises standard components such as a display screen, a data input device for inputting functions, and a storage medium, such as a hard disk or optical drive, for the storage of data.

Interface unit 14, as hereinbefore described, comprises a signal processor 20 and an A/D (analog/digital) interface 22 connected to a transmitter 23.

In the exemplary configuration of FIG. 8, three stand-alone fetal monitoring systems 410, referenced 410*a*, 410*b* and 410*c*, are shown. Each stand-alone fetal monitoring system 410 may be optionally either directly coupled (410*a* and 410*c*) or remotely connected (410*b*) to a main central processing unit (CPU) 416, to which an archiving system 28 is coupled.

Main CPU 416 is similar to the central processing unit 16, described hereinabove with respect to FIG. 1. Main CPU 16 may be used to receive data from and perform the processing functions (instead of the local CPU) relating to data being received from the fetal well-being sensor 12.

Alternatively, main CPU 16 may act as an interface between the fetal monitoring systems 410 and the archive unit 28, to process the traces and data received from each of the stand-alone fetal monitoring systems 410. The archived traces stored in archive unit 28 can be recalled at any time and played back either on monitoring/display unit 18 (connected to main CPU 16) or on the local monitoring/display unit 414.

It will be appreciated by persons skilled in the art that fetal monitoring system 400 may be combined with any of the elements associated with other embodiments previously described hereinabove. For example, a remote display unit 202 and a remote input unit 204, may be coupled to archiving unit 28, as described with respect to the embodiments of FIGS. 6 and 7.

It will be appreciated by persons skilled in the art that the present invention is not limited to what has been particularly shown and described hereinabove. Rather the scope of the present invention is defined only by the claims which follow:

I claim:

1. A system for monitoring the condition of a fetus, the system comprising:
   (a) a plurality of sensors each of said sensors being deployable so as to generate an output indicative of a physiological parameter;
   (b) a processing unit associated with all of said sensors, said processing unit being configured:
      (i) to process said outputs to derive at least one calculated parameter related to fetal well-being, and
      (ii) to apply fetal well-being test criteria to said at least one calculated parameter to identify occurrence of an alarm condition; and
   (c) a monitoring unit associated with said processing unit, said monitoring unit being responsive to identification of an alarm condition to generate an alarm signal,
wherein said fetal well-being test criteria include at least one multiple-level threshold test wherein an alarm condition is identified both when a first of said at least one calculated parameter passes a first threshold level for in excess of a first time period and when said first calculated parameter passes a second threshold level differing from said first threshold for in excess of a second time period longer than said first time period.

2. The system as in claim 1, wherein said first calculated parameter is a score based on at least fetal heart rate variability.

3. The system as in claim 2, wherein said second time period is at least about ½ hour.

4. The system as in claim 2, wherein said processor unit is configured to derive said score of fetal heart rate variability based upon measurements taken during a sliding window of about 5 minutes.

5. The system as in claim 1, further comprising a user input device associated with said processor unit for inputting data associated with a medical treatment being administered, said processor unit being responsive to said data to change said fetal well-being test criteria applied to said at least one calculated parameter.

6. The system as in claim 1, wherein said processor unit includes a database of fetal heart rate patterns indicative of fetal distress, said processor unit being further configured to employ said database in application of said fetal well-being test criteria.

7. The system as in claim 1, wherein said monitoring unit is further configured to display said sensor outputs.

8. The system as in claim 7, further comprising an archiving unit associated with said processor unit, said archiving unit including data storage means and being configured to maintain a record of said sensor outputs, the system being further configured to assume a replay mode in which said record of said sensor outputs is read from said archiving unit and displayed by said monitoring unit.

9. The system as in claim 1, wherein said plurality of sensors are referred to as a first plurality of sensors and are deployable so as to generate an output indicative of a physiological parameter relating to a first fetus, the system further comprising a second plurality of sensors similar to said first plurality of sensors, each sensor of said second plurality of sensors being deployable so as to generate an output indicative of a physiological parameter relating to a second fetus, wherein said processor unit is additionally associated with said second plurality of sensors and is further configured to process outputs from said second plurality of sensors.

10. A system for monitoring the condition of at least one fetus, the system comprising:
   (a) a plurality of sensors each of said sensors being deployable so as to generate an output indicative of a physiological parameter;
   (b) a processing unit associated with all of said sensors, said processing unit being configured:
      (i) to process said outputs to derive at least one calculated parameter related to fetal well-being, and
      (ii) to apply fetal well-being test criteria to said at least one calculated parameter to identify occurrence of an alarm condition;
   (c) a monitoring unit associated with said processing unit, said monitoring unit being responsive to identification of an alarm condition to generate an alarm signal; and
   (d) a user input device associated with said processor unit for inputting data associated with a medical treatment being administered,
wherein said processor unit is responsive to said data to change said fetal well-being test criteria applied to said at least one calculated parameter.

11. A system for monitoring the condition of at least one fetus, the system comprising:

(a) a plurality of sensors each of said sensors being deployable so as to generate an output indicative of a physiological parameter, said plurality of sensors including a fetal heart activity sensor;

(b) a processing unit associated with all of said sensors, said processing unit including a database of fetal heart rate patterns indicative of fetal distress, said processor unit being configured:
  (i) to process said outputs to derive at least a measured fetal heart rate pattern, and
  (ii) to compare said measured fetal heart rate pattern with said fetal heart rate patterns indicative of fetal distress to identify occurrence of an alarm condition; and (c) a monitoring unit associated with said processing unit, said monitoring unit being responsive to identification of an alarm condition to generate an alarm signal.

12. A system for monitoring the condition of a fetus, the system comprising:

(a) a plurality of sensors each of said sensors being deployable so as to generate an output indicative of a physiological parameter;

(b) a processing unit associated with all of said sensors, said processing unit being configured:
  (i) to process said outputs to derive at least one calculated parameter related to fetal well-being, and
  (ii) to apply fetal well-being test criteria to said at least one calculated parameter to identify occurrence of an alarm condition;

(c) a monitoring unit associated with said processing unit configured to display said sensor outputs, said monitoring unit being responsive to identification of an alarm condition to generate an alarm signal; and (d) an archiving unit associated with said processor unit, said archiving unit including data storage means and being configured to maintain a record of said sensor outputs, wherein the system is further configured to assume a replay mode in which said record of said sensor outputs is read from said archiving unit and displayed by said monitoring unit.

* * * * *